US012635991B2

(12) United States Patent

Althobaiti et al.

(10) Patent No.: US 12,635,991 B2

(45) Date of Patent: May 26, 2026

(54) EPIDURAL NEEDLE

(71) Applicant: Imam Abdulrahman Bin Faisal University, Dammam (SA)

(72) Inventors: Murad Althobaiti, Dammam (SA); Nasir Ghazi Hariri, Dammam (SA); Sajid Ali, Dammam (SA); Kamran Hameed, Dammam (SA); Naif Adnan Al-Rubai, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 341 days.

(21) Appl. No.: 18/454,863

(22) Filed: Aug. 24, 2023

(65) Prior Publication Data

US 2025/0064431 A1 Feb. 27, 2025

(51) Int. Cl.
| | |
|---|---|
| *A61B 10/00* | (2006.01) |
| *A61B 17/34* | (2006.01) |
| *A61B 90/00* | (2016.01) |

(52) U.S. Cl.
CPC ...... *A61B 10/0045* (2013.01); *A61B 17/3401* (2013.01); *A61B 2010/0077* (2013.01); *A61B 2090/064* (2016.02)

(58) Field of Classification Search
CPC ............ A61B 10/0045; A61B 17/3401; A61B 2010/0077; A61B 2090/064
See application file for complete search history.

(56) References Cited

U.S. PATENT DOCUMENTS

| | | | |
|---|---|---|---|
| 5,836,914 A | 11/1998 | Houghton | |
| 2015/0342635 A1* | 12/2015 | Tsamir | A61B 17/3476 |
| | | | 604/164.04 |
| 2018/0000348 A1* | 1/2018 | Bishara | A61B 5/6806 |
| 2021/0386452 A1* | 12/2021 | Dick | A61B 5/4896 |

FOREIGN PATENT DOCUMENTS

| | | |
|---|---|---|
| CN | 100581601 C | 1/2010 |
| CN | 106821469 A | 6/2017 |
| CN | 114073569 A | 2/2022 |
| CN | 114224441 A | 3/2022 |
| JP | 2011/147501 A | 8/2011 |

OTHER PUBLICATIONS

Koseki et al. ; Coaxial Needle Insertion Assistant for Epidural Puncture ; IEEE ; Dec. 5, 2011 ; 6 Pages.

* cited by examiner

*Primary Examiner* — Eric J Messersmith
*Assistant Examiner* — Nidhi N Patel
(74) *Attorney, Agent, or Firm* — Oblon, McClelland, Maier & Neustadt, L.L.P.

(57) ABSTRACT

An epidural needle with a mechanism to receive real-time feedback on the location of the epidural needle during insertion process of the epidural needle. In particular, the epidural needle includes a spring and a pair of needles coupled to a force-measuring sensor for a continuous measurement of the force at a tip of the epidural needle as the epidural needle is inserted. The spring is enclosed in a spring section between a lug section and a needle section. The lug section comprises the force-measuring sensor and the needle section comprises a needle to be inserted. The lug section, the spring section and the needle section are axially aligned along an epidural needle axis. A force is transmitted from the needle section through the spring of the spring section to the force-measuring sensor of the lug section.

16 Claims, 5 Drawing Sheets

EPIDURAL NEEDLE

BACKGROUND

Technical Field

The present disclosure is directed to an epidural and/or spinal needle with a mechanism to receive real-time feedback on the location of the epidural needle during the insertion process. In particular, the epidural needle includes a spring and a pair of needles coupled to a force-measuring sensor for a continuous measurement of the force at a tip of the epidural needle as the epidural needle is inserted.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Spinal needles are devices that are used for puncturing the spine to inject medications such as anesthetic medications or chemotherapy drugs into the cerebrospinal fluid. Spinal needles are also used for extracting cerebral spinal fluid (CSF) for diagnosing various health conditions such as cancer, Guillain-Barre syndrome, meningitis and such disorders and/or infections. Medical professionals use spinal needles to inject analgesia and/or anesthetic directly into the CSF, for example, at a point below second lumbar vertebra. Spinal needles are inserted to the spine to reach the CSF through the membranes surrounding the spinal cord, which is only about 4 mm thick.

Conventional spinal needles require high expertise and practice to accurately insert the needle into the cerebral spinal fluid (CSF). Healthcare professionals, such as, medical doctors, rely on their expertise during use of the spinal needles, to estimate when the spinal needle has reached the CSF. Many times, there may be challenges to identify a location to insert the spinal needle to reach the CSF. In an example, it may be challenging for the healthcare professional to identify an accurate point on a back of an obese patient to insert the needle to reach the CSF. Sometimes, the healthcare professional may have to attempt multiple times by trial and error method to reach the CSF. At times, despite best efforts, accidents occur such as accidental puncture due to reflex movement during pricking. Such accidents can cause serious injuries leading to motor issues and sometimes permanent injuries.

Accordingly, it is one object of the present disclosure to provide an epidural needle that provides a user such as a healthcare professional, real-time feedback on the location of the epidural needle during the insertion process, e.g., the tissue environment in which the tip of the needle is embedded or penetrating. In addition, the embodiments disclosed herein employ a force measuring sensor in combination with a spring and dual-needle system for safe and accurate insertion of an epidural needle. The epidural needle disclosed herein reduces number of insertions generally required for an epidural needle and also reduces the associated risks and pain.

SUMMARY

In an embodiment, an epidural needle is described. An epidural needle includes a lug section, a spring section, and a needle section. The spring section is between the lug section and the needle section. The lug section, the spring section and the needle section are axially aligned along an epidural needle axis. The lug section includes a force-measuring sensor mounted on a first end of the lug section. The spring section includes an inner needle, an inner needle holder, and a spring. The inner needle is configured to be fixed in position along the epidural needle axis. The inner needle is attached to a first end of the inner needle holder. The spring is enclosed inside the inner needle holder and is mechanically connected to the inner needle holder.

The needle section includes an outer needle and an outer needle holder. The outer needle is attached to a first end of the outer needle holder and the inner needle is nested inside and rests against an inner wall of the outer needle. A collated force is transmitted from the needle section through the spring of the spring section to the force-measuring sensor of the lug section.

The spring section further includes a pair of stabilizing extensions on either side of the spring aligned parallel to the epidural needle axis. The pair of stabilizing extensions pass through from either side of a first end of the inner needle holder to either side of the first end of the outer needle holder.

The pair of stabilizing extensions are configured to secure and clasp the inner needle holder and outer needle holder Each stabilizing extension of the pair of stabilizing extensions is threaded for accepting a fastening nut. The inner needle holder includes a protrusion on a second end of the inner needle holder. The protrusion at the inner needle holder is in contact with the force-measuring sensor at the lug section.

The inner needle is configured to pass through the outer needle holder and is nested in the outer needle. The inner needle is configured to fit into an inner cavity of the outer needle.

The outer needle holder includes an indentation on a second end of the outer needle holder.

The indentation is configured to insert the first end of the inner needle holder and the inner needle into the outer needle holder.

The force-measuring sensor includes an electrode. The force-measuring sensor is configured to measure a force applied at the lug section of the epidural needle. The force-measuring sensor is configured to measure the collated force transmitted from the needle section.

The lug section and the spring section are configured to separate from the needle section. The needle section is configured to collect a cerebral spinal fluid.

The epidural needle is configured to collect a cerebral spinal fluid.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
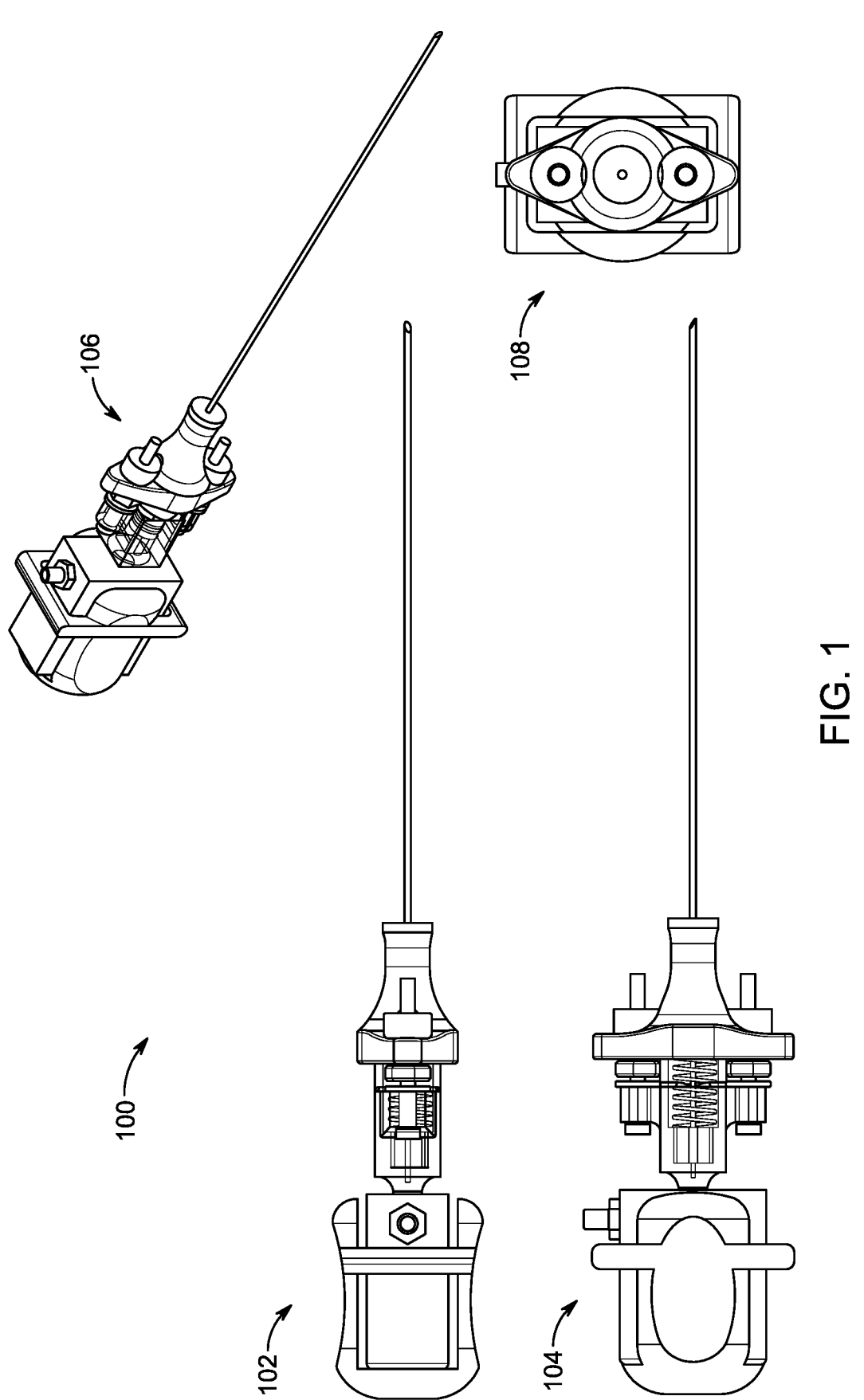
FIG. 1 shows various views of epidural needle, according to some embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Generally, an epidural needle is employed to deliver medication or remove a sample from the epidural space of a patient. The epidural needle may be used for treatment in chronic back pain or to provide anesthesia as well as pain relief during a surgery or childbirth. The medication has to percolate through semi-liquid fat to reach the nerve roots, near specific nerves to decrease pain in a certain part of the patient's body. This process of achieving pain relief through medication is also referred to as an anesthetic block. The dosage required for pain relief cannot be administered at once, due to potential impacts of toxicity with a large dosage of the medication. To avoid such impact, the medication is often administered as an initial dosage and then other subsequent multiple dosages. To achieve the ongoing administration, a catheter can be inserted into the epidural space through the epidural needle to provide sustained or prolonged medication to the patient.

Spinal needles, such as, epidural needles are used to inject analgesia and/or anesthetic directly into the cerebral spinal fluid (CSF). The epidural or spinal needle carrying the medication enters the cerebral spinal fluid or the epidural space through the membranes surrounding the spinal cord, which is only about 4 mm thick. The preferred location for accessing the cerebral spinal fluid sample is generally located at a spinal point below the second lumbar vertebra.

The embodiments herein describe an epidural needle that offers a safe and accurate way to insert and determine extent of insertion into the epidural space. In the embodiments herein, the epidural needle is configured to sense pressure differences during insertion and provide a feedback signal to a healthcare professional when the needle penetrates into the CSF space and/or reaches the cerebral spinal fluid (CSF). As a result, the needle provides a safer option for the patient compared to conventional needles, and can be used with high accuracy avoiding the need for multiple insertions. This will reduce the associated risks.

Turning to the drawings, FIG. 1 illustrates various views of the epidural needle 100, according to some embodiments. View 102 is a side view of the epidural needle 100. View 104 is a top view of the epidural needle 100. View 106 is a perspective view of the epidural needle 100 and a view 108 is a rear view of the epidural needle 100. A high-level construction of the epidural needle 100 is explained in FIG. 2.

Figure 2:
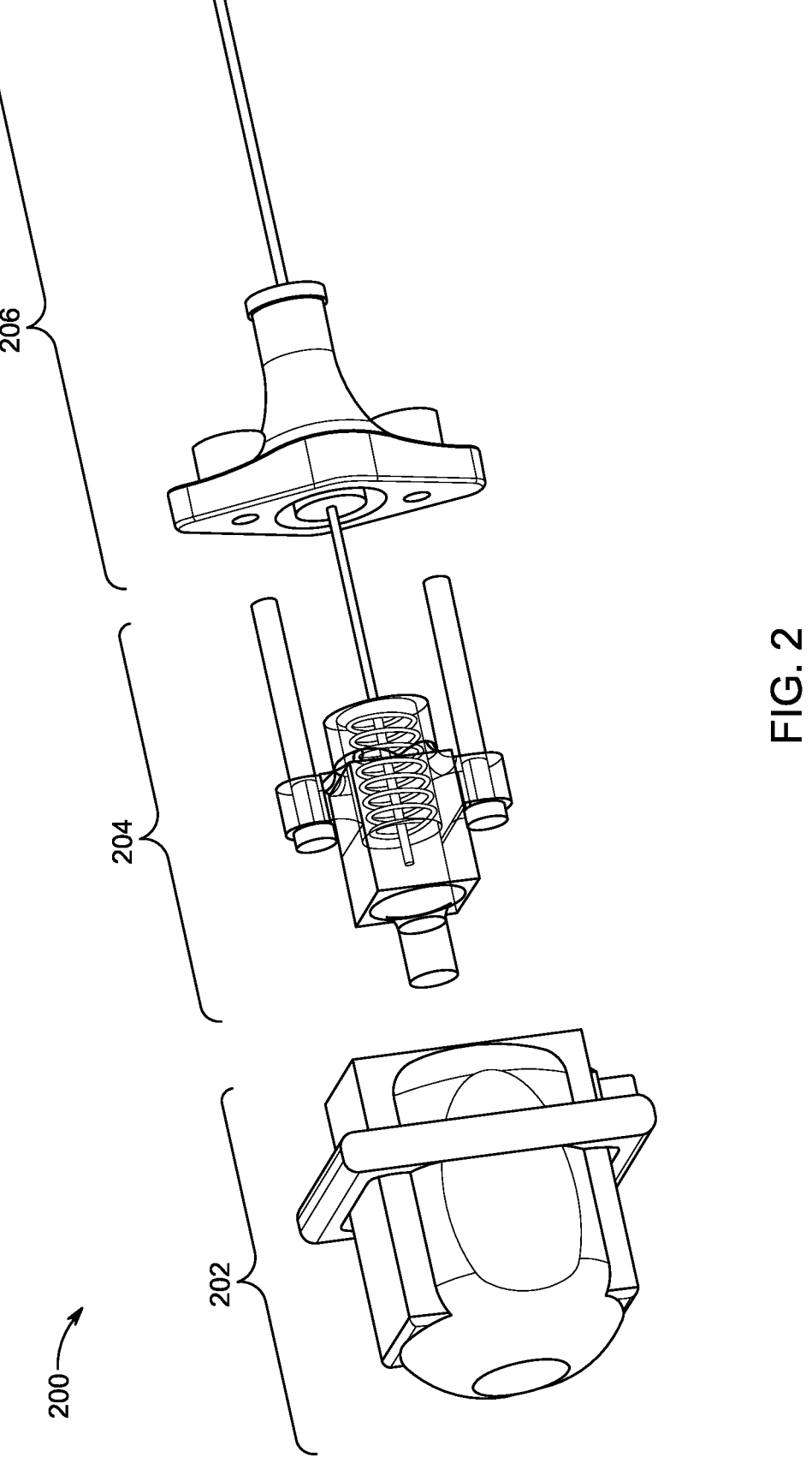
FIG. 2 shows a high-level construction of the epidural needle, according to some embodiments.

FIG. 2 shows a high-level construction of portions of the epidural needle 200, according to some embodiments. The epidural needle 100, as illustrated in FIG. 2 includes three sections: a lug section 202, a spring section 204, and a needle section 206. The spring section 204 is located between the lug section 202 and the needle section 206. The lug section 202, the spring section 204 and the needle section 206 are axially aligned along an epidural needle axis. The lug section 202 includes a housing configured to include a force-measuring sensor. The first end, e.g., distal end, of the lug section 202 is used as a holder 322 of the epidural needle for pressing the epidural needle 100 into the body of a patient, e.g., by application of an insertion force. The lug section 202 also includes a cavity at a second end of the lug section proximal to the spring section for the spring section 204 to be mechanically coupled to the lug section 202.

Figures 3A, 3B:
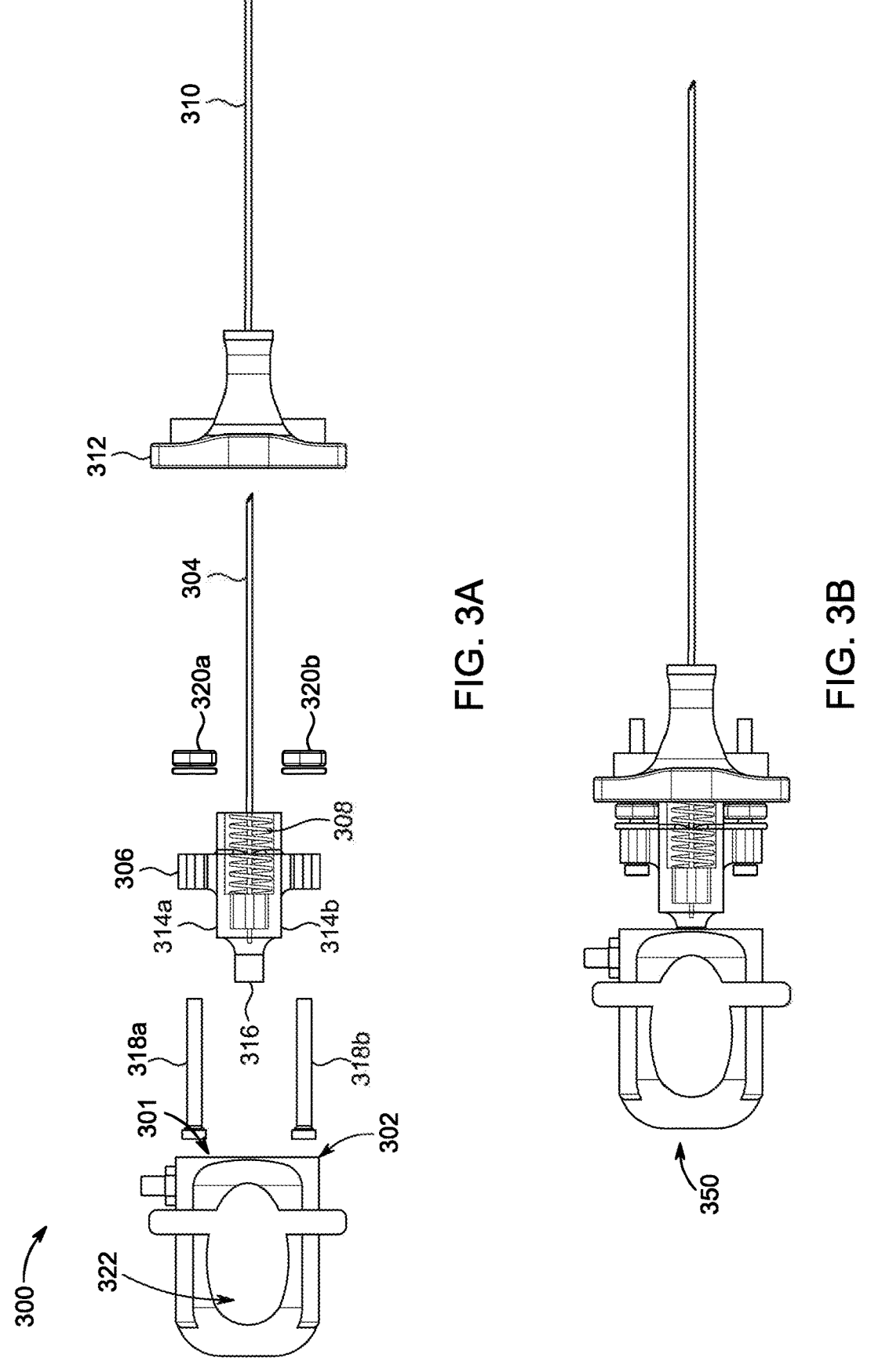
FIG. 3A illustrates a disassembled view of the epidural needle, according to some embodiments.
FIG. 3B shows an assembled view of the epidural needle, according to some embodiments.

The spring section 204 includes an inner needle, an inner needle holder, a spring, and a pair of stabilizing extensions (see FIGS. 3A and 3B). The inner needle is configured to be fixed in position along the epidural needle axis. The inner needle is configured to be nested inside an outer needle of the needle section 206. The needle section 206 includes an outer needle and an outer needle holder. A detailed construction is provided in FIG. 3A and is described below.

FIG. 3A illustrates a disassembled view of the epidural needle 300, according to some embodiments. The epidural needle 300 comprises the three sections as described above, a lug section 202, a spring section 204, and a needle section 206. The first end of the lug section 202 is provided for holding the epidural needle as a holder 322 of the epidural needle during insertion of the epidural needle, for exertion of force to insert the needle. As described, the lug section 202 also includes a housing configured to hold a force-measuring sensor 302. The housing includes a location to hold the force-measuring sensor 302 such that the force-measuring sensor 302 is disposed along the epidural needle axis and at a second end of the lug section 202. The force-measuring sensor 302 is disposed such that the force-measuring sensor 302 experiences all the force during the insertion of the epidural needle 300 into a body. The lug section 202 also includes a cavity 301 at a second end of the lug section for the spring section 204 to be mechanically coupled to the lug section 202. The force-measuring sensor 302 is disposed at the same location on the lug section 202 as the cavity 301 for the spring section 204 to be mechanically coupled to the lug section 202. A force from the spring section 204 transfers to the lug section 202 as the epidural needle is inserted. This transfer of force is from the spring section 204 to the force measuring sensor 302 at the second end of the lug section 202. The cavity 301 is shaped such as to have maximum contact with the proximal end of the spring section, to have an accurate measurement of the transferred force.

In an example embodiment, the shape of the cavity 301 may be cylindrical, and the proximal end corresponding with the first end of the spring section 204 may have a cylindrical shaped protrusion such that the walls and face of the protrusion at the proximal end of the spring section 204 have maximum surface area contact with outer face surface of the cavity 301 of the lug section 202 on connecting the spring section 202 to the lug section 204. In another example embodiment, the shape of the cavity 301 may be conical, and the proximal end of the spring section is preferably such that the protrusion of the spring section 204 has a corresponding conical shape that fits into the conical shape of the cavity 301 of the lug section 202. The force measuring sensor 302 is preferably disposed along all outer edges of the cavity 301 such that the periphery of the protrusion at the proximal end of the spring section 204 in contact with the lug section 202 is in continuous mechanical contact with the force measuring sensor 302 for an accurate measurement of the force transferred from the spring section 204 to the lug section 202. The force-measuring sensor 302 is configured to measure a force applied at the tip of the outer needle of the needle section 206 and transmitted through the outer needle through the spring section 204 to the lug section 202. In an example embodiment, the force-measuring sensor 302 may include an electrode, a strain gauge, load cell, etc.

The housing may also include a measurement unit to obtain measurements from the force-measuring sensor 302. In some examples, the measurement unit may be a mechanical measurement unit. In some examples, the measurement unit is preferably an electronic measurement unit. In some implementations, the housing may also include or be in connection with communication circuitry that is configured to communicate the force measurements to an external device. In some examples, the communication circuitry may be a wired unit coupled with an external device. In some examples, the communication circuitry may be a wireless unit, such as a BLUETOOTH® unit, configured to communicate with the external device. The housing may be made of a thermoplastic or thermoset polymer, metal and the like. In some examples, the external device may be a display screen, to display the force measurement values to the medical practitioner.

The spring section 204 includes an inner needle 304, an inner needle holder 306, a spring 308 and a pair of stabilizing extensions 318a and 318b. The inner needle 304 is held by the inner needle holder 306 such that the inner needle 304 is fixed in position along the epidural needle axis of the epidural needle 100. The inner needle 304 is attached to a first end of the inner needle holder 306. The inner needle 304 may be made of ferrous alloys such as stainless steel, nickel magnetic alloys and the like. The inner needle 304 is extended inside the inner needle holder 306 to a depth of from 0.1 to 0.8× total length of the outer needle, preferably from 0.2-0.6, 0.3-0.5 or about 0.4× total length of the outer needle. The spring 308 is inset inside the inner needle holder 306, wound around the inner needle 304. The inner needle holder is shaped as a circular tube at an end proximal to the first end of the inner needle holder to hold the enclosed spring 308. The second end of the inner needle holder 306 comprises a small protrusion 316. The protrusion 316 is shaped to match the shape of the cavity 301 at the second end of the lug section 202. The protrusion 316 may be cylindrical if the cavity of the lug section 202 is shaped cylindrical. The protrusion 316 may be conical if the cavity of the lug section 202 is shaped conical. The inner needle holder 306 further comprises two circular openings, one on each side of the circular tube enclosing the spring 308. The pair of stabilizing extensions 318a, 318b pass through the two circular openings of the inner needle holder 306. The spring 308 may be stainless steel spring, a copper-based spring, a high-carbon steel, etc. The spring 308 may be with a spring constant 'K'.

Figure 5:
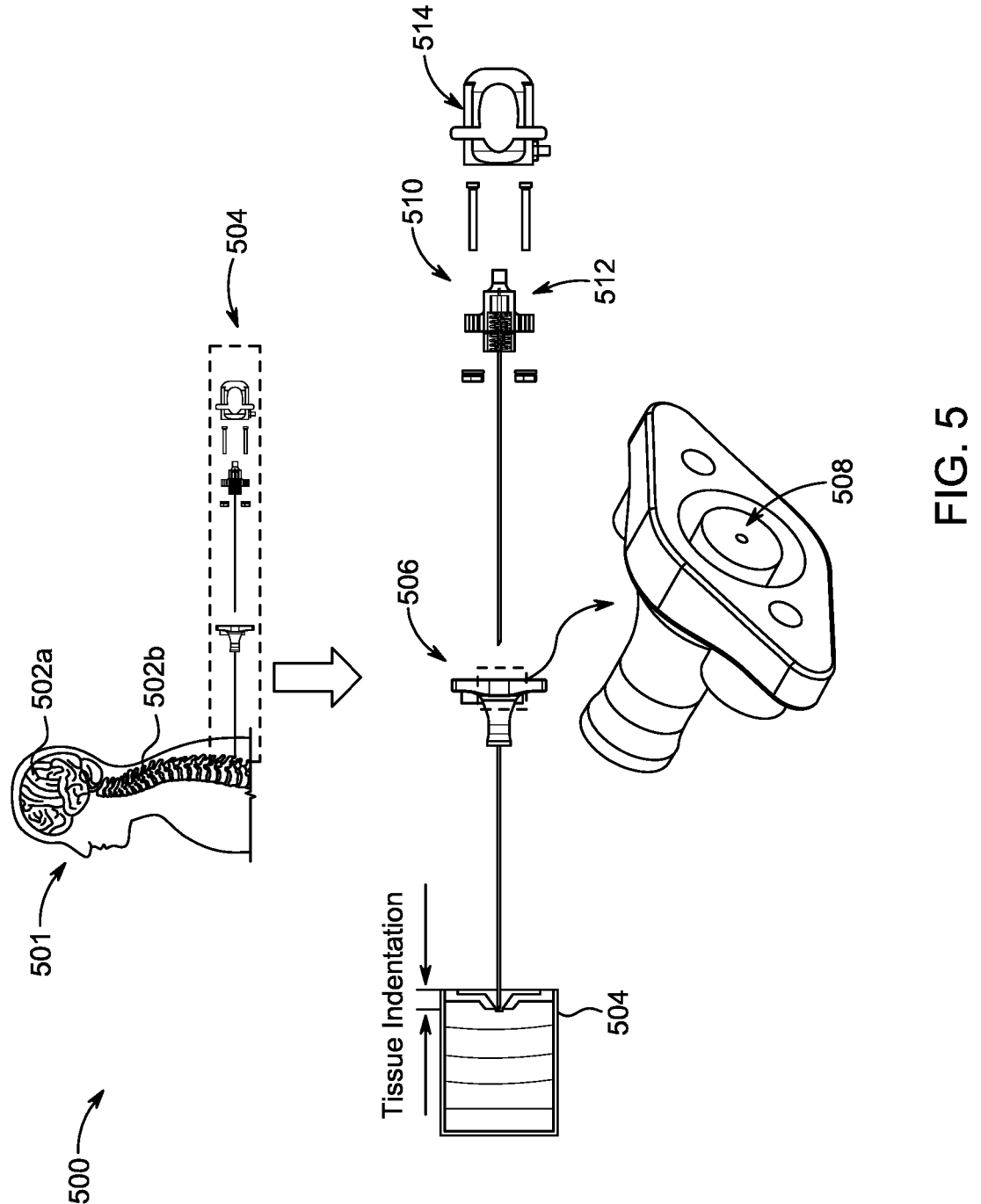
FIG. 5 shows detaching a lug section and a spring section from a needle section of the epidural needle, according to some embodiments.

The inner needle 304 is configured to fit into an inner cavity of the outer needle 310 from the tip end of the inner needle 304. The inner needle 304 enters an outer needle holder 312 from a second end of the inner needle 304, and is nested inside and rests against an inner wall of the outer needle 310. The length of the inner needle 304 is smaller than the length of the outer needle 310, the length of the inner needle 304 ranging from about a quarter up to half of the length of the outer needle 310. The outer needle holder 312 comprises a central circular shape surrounded by a circular ring-like space to fit the circular tube of the spring section 204 enclosing the spring 308 (this is illustrated in FIG. 5 by numeral 508). Each of the pair of stabilizing extensions 318a, 318b is on either side of the spring 308 aligned parallel to the epidural needle axis. The pair of stabilizing extensions 318a, 318b pass through from the circular openings on either side of a first end of the inner needle holder 306 to circular openings on either side of a first end of the outer needle holder 312. The pair of stabilizing extensions 318a, 318b are configured to secure and clasp the inner needle holder to the outer needle holder 312. Each stabilizing extension of the pair of stabilizing extensions 318a, 318b is preferably threaded for accepting each fastening nut of a pair of fastening nuts 320a, 320b. In some examples, the pair of stabilizing extensions 318a and 318b may be screws. The outer needle holder 312 further comprises a cylindrical extension at the second end of the outer needle holder 312 to which the outer needle 310 is attached. In an example, the pair of fastening nuts 320a, 320b may be compression fasteners The needle section 206 includes the outer needle 310 and the outer needle holder 312. The outer needle 310 is attached to a first end of the outer needle holder 312, and is preferably fixedly attached thereto. The outer needle holder 312 may be a metal, thermoset or thermoplastic polymer and the like. The outer needle holder 312 includes an indentation on a second end of the outer needle holder 312 such that the outer needle 310 is firmly held along the epidural needle axis and allows inserting the first end of the inner needle holder 306 and the inner needle 304 into the outer needle holder 312. A second end of the outer needle 310 is a tip of the outer needle 310. The outer needle 310 may be a hollow metal tube with a sharp and pointed tip for easy tissue penetration and is preferably straight along its entire length. The hollow tube accommodates the inner needle 304. The outer needle 310 is inserted into the membranes of the patient up to the cerebral spinal fluid. The inner needle 304 is fixed in position along the epidural needle axis. The outer needle 310 may be made of stainless steel, nickel magnetic alloys, and the like.

FIG. 3B shows an assembled view 350 of the epidural needle 100, according to some embodiments. In some example embodiments, the spring section 204 is coupled with the needle section 206 by inserting the inner needle 304 into the outer needle 310 through the outer needle holder 312. The spring section 204 is secured and clasped with the needle section 206 through the pair of stabilizing extensions 318a, 318b using, for example, fastening nut and bolt mechanism and/or compression fittings provided by fasteners 318a, 318b and their corresponding fastening nuts 320a, 320b. Also, the lug section 202 and the spring section 204 are coupled in the cavity of the housing 322 of the lug section 202 by inserting the protrusion 316 of the spring section 204 into the cavity of the housing. In some examples, the coupling may be performed through adhesives or welding. The assembled view 350 of the epidural needle 100 is shown in FIG. 3B. In aspects, the lug section 202 and the spring section 204 are configured to be separated from the needle section 206 using the stabilizing extensions 318a and 318b.

Figure 4:
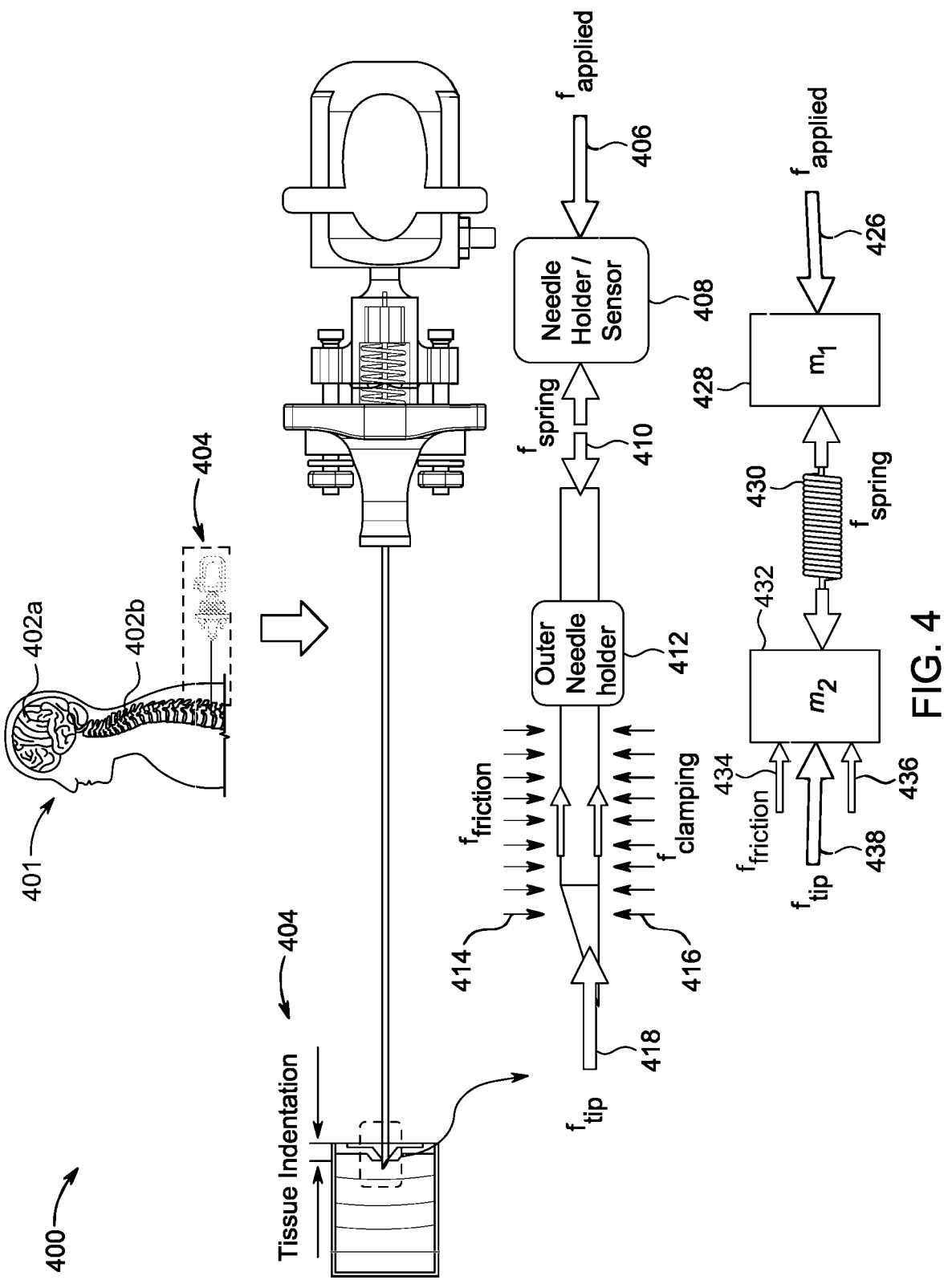
FIG. 4 shows an operation of the epidural needle, according to some embodiments.

FIG. 4 shows an operation of the epidural needle, according to some embodiments. The epidural needle 100 is configured to function as a spring-pushed-based device, where the spring is in between the force measuring sensor 302 and the inner needle 304. The outer needle holder 312 in which the outer needle 310 is placed is connected to the force-measuring sensor 302 through the spring 308. When in use 404, for example, on a human 401 brain 402a and/or spine 402b system, the outer needle is inserted into the skin and further into membranes protecting the spine. During insertion, the force-measuring sensor in the lug section 408 experiences and measures an applied insertion force on the lug section 408 (referred to as $f_{applied}$ 406). This force is transmitted from the holder at the lug section 408, first to the spring (referred to as $f_{spring}$ 410) and then to the outer needle holder 412, and to the outer needle tip (referred to as $f_{up}$ 418). As the tip of the needle is pushed into the tissue and membranes, creating tissue indentation and then penetration, the outer needle is subject to forces from a tip of the outer needle that allow it to penetrate, as well as friction force on needle's outer surface during the sliding motion within the tissue. The force at the tip is referred to as $f_{tip}$ 418. While penetrating the membranes and tissues, the epidural needle 100 faces friction resistance (referred to as $f_{friction}$ 414 and $f_{clamping}$ 416) from the different tissues before it reaches the CSF. The resistance experienced by the needle is experienced by the force-measuring sensor at the lug section 408 via the spring (referred to as $f_{spring}$ 410) at the inner needle holder. Once the outer needle enters the CSF, the force-measuring sensor records a significant pressure drop, e.g., a drop in measured force. This pressure drop is used as an indication that the needle has reached the epidural space. At this point, the lug section, and the spring section along with the inner needle are removed, preferably as a single assembly, and the CSF sample can be collected accordingly. Overall, the force-measuring sensor experiences and measures $f_{applied}$, $f_{tip}$, and $f_{friction}$ based on a combined force that transmitted from the needle section through the spring of the spring section to the force-measuring sensor of the lug section.

Thus, the forces governing dynamics of the epidural needle 100 are estimated by:

$$\text{Mass 1: } f_{spring} - f_{applied} = m_1 x_1, \tag{1}$$

$$\text{Mass 2: } f_{tip} + f_{friction} - f_{spring} = m_2 x_2. \tag{2}$$

where, mass $m_1$ 428 is the lug section of the epidural needle and mass $m_2$ 432 is the outer needle holder of the epidural needle. The spring is positioned in the inner needle holder between the outer needle holder and the lug section.

FIG. 5 shows the disassembly of the epidural needle 100 after the tip of the outer needle reaches the cerebral spinal fluid. Upon reaching the desired location for the cerebral fluid, the pair of fastening nuts 510, 512 (320a, 320b) are removed. This allows detaching the lug section 514 (202) and the spring section 204 from the needle section 206 at the outer needle holder 312. The detached needle section is as shown as 508 in FIG. 5. The detachment is performed when the needle section 206 is securely held to the body at tissue indent 504. Once the inner needle 304 is removed, while securing the outer needle in its place, the cerebral fluid may be allowed to pass through the outer needle 310 to the end of the outer needle holder 312 as shown in FIG. 5

Although FIG. 1-FIG. 5 show the pair of stabilizing extensions 318a, 318b, there may be more than a pair of stabilizing extensions 318a, 318b. Also, though nut and bolt mechanisms are shown, other coupling techniques not described herein can be used.

The embodiments herein offer a safe and accurate way of delivering medication to the epidural space and for removing CSF samples from the epidural space, for treatments such as, chronic back pain treatment, a method to provide anesthesia or pain relief during childbirth. Conventional needles need a high level of expertise and practice to rightly insert the epidural needle into the cerebral spinal fluid. The embodiments disclosed herein reduce risks associated with multiple insertions of the needle and the risk of bleeding or nerve damage that occurs in conventional needles.

The epidural needle 100 ensures that the outer needle 310 is within the epidural space. Otherwise, the pain relief may be ineffective or inadequate due to improper placement of catheter. The embodiments herein support real-time dynamic monitoring of force experienced by the epidural needle 100 to a healthcare professional while providing a less painful experience to patients. Although the application is described for epidural purposes, the embodiments herein can be expanded for medical applications such as biopsy and epidural anesthesia where needle positioning accuracy is crucial. The epidural needle 100 may be used to provide real-time feedback for successful painless insertion of spinal needles avoiding any severe accidents. The epidural needle 100 may reduce dependencies on experts, and through automated measurements, experience of the medical procedure can be made more comfortable.

Numerous modifications and variations of the present disclosure are possible in light of the above teachings. It is therefore to be understood that within the scope of the appended claims, the invention may be practiced otherwise than as specifically described herein.

The invention claimed is:

1. An epidural needle, comprising:
   a lug section, a spring section, and a needle section wherein the spring section is between the lug section and the needle section and wherein the lug section, the spring section and the needle section are axially aligned along an epidural needle axis;
   wherein the lug section comprises a force-measuring sensor mounted on a first end of the lug section and has a cavity at a second end of the lug section;
   wherein the spring section comprises a protrusion, an inner needle, an inner needle holder, and a spring, wherein the inner needle is fixed in position along the epidural needle axis, wherein the inner needle is attached to a first end of the inner needle holder, wherein the spring is inset inside the inner needle holder and is mechanically connected to the inner needle holder;
   wherein the needle section comprises an outer needle and an outer needle holder, wherein the outer needle is attached to a first end of the outer needle holder;
   wherein the inner needle is nested inside and rests against an inner wall of the outer needle;
   wherein the protrusion of the spring section is shaped to match the cavity of the lug section and the spring section is mechanically coupled to the lug section;
   wherein the protrusion of the spring section is in physical contact with the force-measuring sensor at the lug section; and
   wherein the force-measuring sensor is configured to measure a force applied to a tip of the outer needle and transmitted through the outer needle through the spring of the spring section through the protrusion of the spring section to the force-measuring sensor of the lug section.

2. The epidural needle of claim 1, wherein the inner needle holder comprises two circular gaps openings externally at either side of the inner needle holder.

3. The epidural needle of claim 2, wherein the spring section further comprises:

a pair of stabilizing extensions on either side of the spring aligned parallel to the epidural needle axis, wherein the pair of stabilizing extensions pass through from the two circular openings at the inner needle holder and two circular openings at a second end of the outer needle holder to the first end of the outer needle holder.

4. The epidural needle of claim 3, wherein the pair of stabilizing extensions are configured to secure and clasp the inner needle holder and outer needle holder.

5. The epidural needle of claim 3, wherein each stabilizing extension of the pair of stabilizing extensions is threaded for accepting a fastening nut.

6. The epidural needle of claim 1, wherein the inner needle is in physical contact with the outer needle.

7. The epidural needle of claim 1, wherein a length of the inner needle is from 0.3 up to 0.8 times a length of the outer needle.

8. The epidural needle of claim 1, wherein the outer needle holder comprises an indentation on the second end of the outer needle holder.

9. The epidural needle of claim 8, wherein the indentation is configured to permit insertion of the first end of the inner needle holder and the inner needle into the outer needle holder.

10. The epidural needle of claim 1, wherein the force-measuring sensor comprises an electrode.

11. The epidural needle of claim 1, wherein the force-measuring sensor is configured to measure an applied force at the lug section of the epidural needle.

12. The epidural needle of claim 1, wherein the force-measuring sensor is configured to measure the force transmitted from the needle section.

13. The epidural needle of claim 1, wherein the lug section and the spring section are configured to separate from the needle section.

14. The epidural needle of claim 1, wherein the needle section is configured to collect a cerebral spinal fluid.

15. The epidural needle of claim 1, wherein the epidural needle is configured to collect a cerebral spinal fluid.

16. The epidural needle of claim 1, wherein protrusion of the spring section is fittingly engaged with the cavity of the lug section.

* * * * *